(12) United States Patent
Cheng et al.

(10) Patent No.: US 7,193,007 B2
(45) Date of Patent: Mar. 20, 2007

(54) ENVIRONMENT RESPONSIVE GELLING COPOLYMER

(76) Inventors: Yu-Ling Cheng, 1379 Glenburnie Road, Mississauga (CA) L5G 3C7; Hai-Hui Lin, 3819 Parkwood Ct., Loveland, OH (US) 45140

( * ) Notice: Subject to any disclaimer, the term of this patent is extended or adjusted under 35 U.S.C. 154(b) by 432 days.

(21) Appl. No.: 10/221,084

(22) PCT Filed: Mar. 15, 2001

(86) PCT No.: PCT/CA01/00325

§ 371 (c)(1),
(2), (4) Date: Jun. 9, 2003

(87) PCT Pub. No.: WO01/68768

PCT Pub. Date: Sep. 20, 2001

(65) Prior Publication Data

US 2005/0020719 A1 Jan. 27, 2005

Related U.S. Application Data

(60) Provisional application No. 60/189,489, filed on Mar. 15, 2000.

(51) Int. Cl.
*C08F 290/04* (2006.01)
*C08L 53/00* (2006.01)

(52) U.S. Cl. .................... 524/504; 524/505; 524/916; 523/105; 424/486

(58) Field of Classification Search ............... 524/504, 524/505, 916; 523/105; 424/486
See application file for complete search history.

(56) References Cited

U.S. PATENT DOCUMENTS

| | | | |
|---|---|---|---|
| 4,938,763 A | 7/1990 | Dunn et al. | 604/891.1 |
| 4,942,035 A * | 7/1990 | Churchill et al. | 514/15 |
| 5,278,201 A | 1/1994 | Dunn et al. | 523/113 |
| 5,278,204 A | 1/1994 | Tojo et al. | 523/212 |
| 5,340,849 A | 8/1994 | Dunn et al. | 523/113 |
| 5,410,016 A | 4/1995 | Hubbell et al. | 528/354 |
| 5,688,855 A | 11/1997 | Stoy et al. | 524/505 |
| 5,733,950 A | 3/1998 | Dunn et al. | 523/113 |
| 5,739,176 A | 4/1998 | Dunn et al. | 523/113 |
| 5,744,153 A | 4/1998 | Yewey et al. | 424/426 |
| 5,759,563 A | 6/1998 | Yewey et al. | 424/426 |
| 6,201,065 B1 * | 3/2001 | Pathak et al. | 525/90 |
| 6,350,812 B1 | 2/2002 | Vert et al. | 524/845 |
| 6,486,213 B1 * | 11/2002 | Chen et al. | 514/772.1 |

FOREIGN PATENT DOCUMENTS

| | | |
|---|---|---|
| FR | 2 741 628 | 5/1997 |
| WO | WO 95/24430 | 9/1995 |
| WO | WO 97/05185 | 2/1997 |
| WO | WO 99/07343 | 2/1999 |
| WO | WO 00/00222 | 1/2000 |
| WO | WO 00/69942 | 11/2000 |

OTHER PUBLICATIONS

Hoffman, Artifical Organs, 19(5), 458-467, 1995.*
Nagahara et al., *Polymer Gels and Networks*, 4: (2) pp. 111-1127, (1996) "Hydrogel Formation Via Hybridization of Oligonucleotides Derivatized in Water-Soluble Vinyl Polymers."
Miyata et al. *Macromolecules*, 32: (6) pp. 2082-2084, (1999) "Preparation of an Antigen-Sensitive Hydrogel Using Antigen-Antibody Bindings."
Miyata, *Nature*, 399: 6738, pp. 766-769, (1999) "A Reversibly Antigen-Responsive Hydrogel."
Petka et al., *Science*, 281: 5375, pp. 389-392, (1998), "Reversible Hydrogels from Self-Assembling Artificial Proteins."

(Continued)

*Primary Examiner*—Tae H Yoon
(74) *Attorney, Agent, or Firm*—Thomas M. Saunders; Brown Rudnick Berlack Israels LLP

(57) ABSTRACT

The invention relates to a gelable copolymer composition comprising a copolymer in a solvent. The copolymer has the structure A(B)n, wherein the core (A) is soluble in the solvent, the arms (B) are convertible between soluble and insoluble in the solent depending on an environmental condition, and n>1. The composition forms a gel under environmental conditions in which B is insoluble, through formation of B aggregates. Block copolymers comprising polyethylene glycol (PEG) and poly(N-iso-propylacryla-mide) (PNIPAAm) having a liquid form at ambient temperature under aqueous conditions and a gel form at body temperature are disclosed. Copolymer compositions according to the invention can be used to form in situ implants useful in slow-release formulations of biologically active molecules

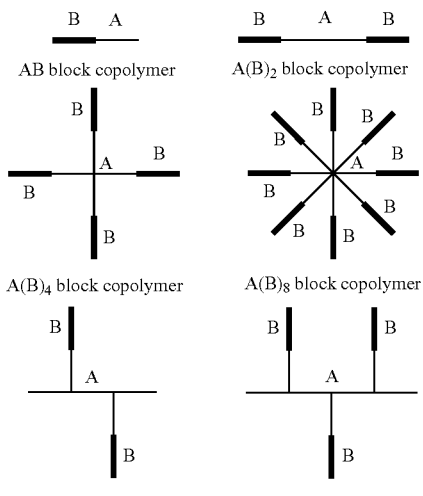

16 Claims, 7 Drawing Sheets

OTHER PUBLICATIONS

Cabana et al., *Journal of Colloid and Interface Science*, 190, pp. 307-312 (1997), "Study of the Gelation Process of Polyethylene Oxide$_a$-Polypropylene Oxide$_b$-Polyethylene Oxide$_a$ Copolymer (Poloxamer 407) Aqueous Solutions."

Jeong et al., *Journal of Controlled Release*, 62, pp. 109-114 (1999), "New Biodegradable Polymers for Injectable Drug Delivery Systems."

Jeong et al., *Macromolecules*, 32: 21, pp. 7064-7069, (1999), "Thermoreversible Gelation of PEG-PLGA-PEG Triblock Copolymer Aqueous Solutions."

Jeong et al., *Nature*, 388, pp. 860-862, (1997), "Biodegradable Block Copolymers as Injectable Drug-Delivery Systems."

Capello et al., *Journal of Controlled Release*, 53, pp. 105-117, (1998), "In-Situ Self-Assembling Protein Polymer Gel Systems for Administration, Delivery, and Release of Drugs."

Yoshioka et al., *J.M.S. Pure Appl. Chem.*, A31: (1) pp. 109-112, (1994), "Preparation of Poly (*N*-Isopropylacrylamide)-*b*-Poly(Ethylene Glycol) And Calorimetric Analysis of its Aqueous Solution."

Yoshioka et al., *J.M.S. Pure Appl. Chem.*, A31: (1) pp. 113-120, (1994), "A Synthetic Hydrogel With Thermoreversible Gelation. I. Preparation And Rheological Properties."

Yoshioka et al., *J.M.S. Pure Appl. Chem.*, A31: (1) pp. 121-125, (1994), "A Synthetic Hydrogel With Thermoreversible Gelation. II. Effect of Added Salts."

Kaneko, *Macromolecules*, 31: pp. 6099-6105, (1998), "Rapid Deswelling Response of Poly(*N*-isopropylacrylamide) Hydrogels by the Formation of Water Release Channels Using Poly (ethylene oxide) Graft Chains."

Topp et al., *Macromolecules*, 30: pp. 8518-8520, (1997), "Thermosensitive Micelle-Forming Block Copolymers of Poly (ethylene glycol) and Poly (*N*-isopropylacrylamide)."

Virtanen et al., *Macromolecules*, 33: pp. 336-341, (2000), "Grafting of Poly (*N*-isopropylacrylamide) with Poly(ethylene oxide) under Various Reaction Conditions."

Newman et al., *Journal of Physical Chemistry*, 60: pp. 648-656, (1956), "Reversible Association of Cellulose Nitrate in Ethanol."

Kudaibergenov et al., *Macromol. Rapid Commun.* 16, pp. 855-860, (1995), "Temperature-Responsive Swelling and Deswelling of the Copolymers From Vinyl Ether of Ethylene Glycol and Butyl Vinyl Ether."

Zhongli et al., *Radiat. Phys. Chem.*, 42, Nos. 4-6, pp. 959-962, (1993), "A Study on the Deswelling Behaviour of a Thermo-Responsive Hydrogel Prepared by Radiation Polymerizations."

Nishimura et al., *Macromol. Symp.*, 120: pp. 303-313, (1997), "Temperature-Responsive Hydrogels from Cellulose."

Sarkar, *Journal of Applied Polymer Science*, 24: pp. 1073-1087, (1979), "Thermal Gelation Properties of Methyl and Hydroxypropyl Methylcellulose."

Hvidt et al., *Journal of Physical Chemistry*, 98: pp. 12320-12328, (1994), "Micellization and Gelation of Aqueous Solutions of a Triblock Copolymer Studied by Rheological Techniques and Scanning Calorimetry."

Almgren et al., *Colloid Polymer Science*, 273:2, pp. 2-15, (1995) "Self-Aggregation and Phase Behavior of Poly(ethylene oxide)-Poly(propylene oxide)-Poly(ethylene oxide) Block Copolymers in Aqueous Solution."

\* cited by examiner

B—C—A—C—B

A

B

A

B (a) AB (b) A(B)$_2$ (c) A(B)$_4$ (d) A(B)$_8$ $C_{min}$ is the minimum gelation concentration, below which no gel forms

ENVIRONMENT RESPONSIVE GELLING COPOLYMER

CROSS REFERENCE TO RELATED APPLICATIONS

This application claims priority from PCT/CA01/00325 filed Mar. 15, 2001 and U.S. Provisional Application Ser. No. 60/189,489 filed Mar. 15, 2000.

FIELD OF THE INVENTION

The present invention relates generally to copolymers. More particularly, the present invention relates to polymers having properties responsive to environmental changes.

BACKGROUND OF THE INVENTION

Block and graft copolymers are used for a variety of physiological and industrial applications. The solubility of a copolymer in a particular solvent depends inter alia on the characteristics of the monomeric components incorporated into the copolymer.

Polymers capable of gelation induced by environment changes are known. Solvent-induced gelation has also been exploited as a mechanism for producing in situ gelable materials. The solvent-induced gelation concept employs a polymer that is soluble in a non-aqueous solvent, but insoluble in water. When a non-aqueous solution of such a polymer is injected into an aqueous environment, the non-aqueous solvent is exchanged for water and the polymer precipitates, forming a solid mass in situ. Solvent-induced gelation systems have the disadvantage that the initial fluid form of the polymer is formed in a solvent other than the solvent in which the gel eventually forms. U.S. Pat. No. 5,744,153 (Apr. 28, 1998) and U.S. Pat. No. 5,759,563 (Jun. 2, 1998), both to Yewey et al., describe a composition for in situ formation of a controlled drug release implant based on the solvent-induced gelation concept.

A series of patents to Dunn et al. also describe a solvent-induced gel composition (U.S. Pat. No. 5,739,176 issued Apr. 14, 1998; U.S. Pat. No. 5,733,950 issued Mar. 31, 1998; U.S. Pat. No. 5,340,849 issued Aug. 23, 1994; U.S. Pat. Nos. 5,278,201 and 5,278,204 both issued Jan. 11, 1994; and U.S. Pat. No. 4,938,763 issued Jul. 3, 1990). The composition includes a water-insoluble polymer and a drug solubilized in an organic solvent carrier. When the composition is injected into a physiological (aqueous) environment, such as a human subject, the polymer precipitates to form a solid mass. Solvent-induced gel compositions have the disadvantage that an organic solvent is injected into a subject merely to carry the polymer and drug in a liquid form. Thus, the organic solvent must subsequently be metabolized or cleared by the body.

Self-assembling hydrogels have been receiving increasing attention in the last few years, both for their intrinsic scientific interest, and for their potential clinical and non-clinical applications. A number of elegant mechanisms for self-assembling hydrogels have been proposed. Nagahara et al. showed that gels can be formed by complexation between complementary oligonucleotides grafted onto hydrophilic polymers (Polymer Gels and Networks, 4: (2) 111–127, 1996). Miyata et al. prepared antigen sensitive hydrogels based on antigen-antibody binding (Miyata et al., Macromolecules, 32: (6) 2082–2084, 1999; Miyata, Nature, 399: (6738) 766–769, 1999). Petka et al. illustrated a gelation mechanism using triblock copolymers containing a central hydrophilic core and terminal leucine zipper peptide domains (Science, 281: (5375) 389–392, 1998). The terminal domains form coil-coil dimers or higher order aggregates to provide crosslinking when cooled from above its pH-dependent melting point. Thermoreversibility was demonstrated with some hysteresis due to the slow kinetics of coil-coil interactions.

Triblock copolymers having a central hydrophobic poly (propylene oxide) (PPO) segment and hydrophilic poly (ethylene oxide) (PEO) segments attached at each end are commercially available. The aqueous solution of these triblock copolymers (PEO-PPO-PEO) have a fluid consistency at room temperature, and turn into weak gels when warmed to body temperature by forming oil-in-water micelles in aqueous solution. The gelation of the polymer is believed to occur via the aggregation of the micelles (Cabana, et al., J. Coll. Int. Sci., 190 (1997) 307).

A group led by S. W. Kim have reported the development of thermosensitive biodegradable hydrogels (Jeong et al., J. Controlled Release, 62 (1999) 109–114; Jeong et al., Macromolecules, 32: (21) 7064–7069, 1999; Jeong et al., Nature, 388 (1997) 860–862). These hydrogels are block copolymers of PEO and poly(L-lactic acid) (PLLA) in either a di-block architecture PEO-PLLA, or a tri-block architecture PEO-PLLA-PEO. They also report triblock copolymers of poly(ethylene oxide) and poly(lactide-co-glycolide) (PLGA) having the architecture PEO-PLGA-PEO. Aqueous solutions of these polymers were reported to undergo temperature-sensitive phase transitions between fluid solution and gel phases. In aqueous solution, these polymers form micelles composed of hydrophobic cores (either PLGA or PLLA) and hydrophilic surfaces (PEO). Gelation is believed to be due to the aggregation of micelles driven by hydrophobic interactions. This group has also discussed the synthesis of PEO copolymers in multi-armed star shaped architectures having polycaprolactone (PCL) or PLLA chains attached to the PEO arms.

Another class of in situ gelable materials is based on polymers made from proteins, or "protein polymers". Cappello, et al. (J Controlled Release 53 (1998) 105–117) reported gel-forming block copolymers based on repeating amino acid sequences from silk and elastin proteins. When heated to body temperature, the proteins self-assemble via a hydrogen bond mediated chain crystallization mechanism to form an irreversible gel. The gelation occurs over a relatively long time period of more than 25 minutes.

Although a variety of gelling or precipitatable polyethylene glycol/poly(N-isopropylacrylamide) copolymers have been synthesized, none was designed and synthesized with in situ gelation applications in mind. See, for example Yoshioka et al., J. M. S Pure Appl. Chem., A31: (1) 109–112, 1994; Yoshioka, J. M. S. Pure Appl. Chem., A31: (1) 113–120, 1994; Yoshioka, J. M. S Pure Appl. Chem., A31: (1) 121–125, 1994; Kaneko, Macromolecules, 31: 6099–6105, 1998; Topp, et al., Macromolecules, 30: 8518–8520, 1997; and Virtanen, Macromolecules, 33: 336–341, 2000.

Topp et al. disclose block copolymers of PEG and PNIPAAm having the structure of either PNIPAAm-PEG or PNIPAAm-PEG-PNIPAAM which form spherical micelles in aqueous solution (Macromolecules, 30: 8518–8520, 1997). The block copolymers were synthesized by the $Ce^{+4}$ initiated attachment of NIPAAm monomers onto the hydroxyl terminals of PEG chains. It was shown that as PNIPAAm segments grew in length during synthesis, micelles having a PNIPAAm core and PEG corona were formed, and the polymerization of PNIPAAm chains continued in the core of the micelles. The copolymers formed by Topp et al. are of a form appropriate for use in a surfactant composition for drug loaded micelles. However, micelles are isolated entities having no load bearing characteristics, do not form gels, and the formation of micelles is associated with a dilute solution state.

The block copolymers formed by Topp et al. consisted of compositions with PNIPAAm to PEG mass ratios ($M_{n,PNIPAAm}/M_{n,PEG}$) ranging from about 0.14 to 0.48, and they found that block copolymers with a $M_{n,PNIPAAm}/M_{n,pEG}$ ratio exceeding 1/3 show aggregation in water at temperatures below the lower critical solution temperature (LCST) at which a solubility change occurs, and thus are less useful for micelle formation than copolymers with ratios less than 1/3.

There is a need for a gelable polymer that is responsive to environmental changes other than solvent exchange. Further, there is a need for a gelable polymer composition capable of reversibly forming a strong gel.

SUMMARY OF THE INVENTION

It is an object of the present invention to provide a gelable polymer and composition which obviate or mitigate at least one disadvantage of previous gelable polymer systems.

In a first aspect, the present invention provides a gelable composition comprising a copolymer and a solvent, the copolymer having the structure A(B)n, wherein A is soluble in the solvent, B is convertible between soluble and insoluble in the solvent depending on an environmental condition, and n is greater than 1, the composition being convertible from liquid to gel under an environmental condition where B is insoluble. Optionally, the composition according to the invention may additionally comprise an architecturally different copolymer, so that $n_{avg}$ for all copolymers present in the composition is greater than 1.

In a further embodiment, there is provided a gelable copolymer having the structure A(B)n, wherein A is soluble in a desired solvent, B is convertible between soluble and insoluble in the desired solvent depending on an environmental condition, n is greater than 1, and A(B)n forms a gel in the solvent under an environmental condition where B is insoluble.

In further aspect, the present invention provides a gelable copolymer comprising a core selected from compounds soluble in a desired solvent, and arms selected from compounds convertible between soluble and insoluble in the desired solvent depending on an environmental condition, wherein the copolymer forms a gel in the solvent under an environmental condition where the arms are insoluble.

The invention further relates to an in situ forming implant comprising a gelable composition as described above, wherein the solvent is aqueous and the environmental condition comprises heating to a temperature between ambient temperature and body temperature.

The invention also provides a process for forming a gelable composition comprising the steps of: (i) forming a copolymer having the structure A(B)n, wherein A is soluble in a solvent of interest, B is convertible between soluble and insoluble in the solvent depending on an environmental condition, and n is greater than 1; (ii) solubilizing said copolymer in the solvent in an amount adequate to convert the composition from liquid to gel under an environmental condition where B is insoluble.

According to an embodiment of the invention, there is also provided a process for forming an in situ forming implant comprising a gelable composition as described herein, wherein the solvent is aqueous and the environmental condition comprises heating to a temperature between ambient temperature and body temperature.

Advantageously, the gel-forming polymer according to the invention does not require a solvent exchange to convert between a fluid solution and a gel. Thus, the polymer can be prepared and utilized in a single solvent system.

Other aspects and features of the present invention will become apparent to those skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The invention relates to a gelable copolymer, and to a copolymer composition that undergoes structural changes in response to changes in the environment. Within the composition, the inventive copolymer undergoes a phase transition from liquid to gel in response to changes in an environmental parameter such as, for example temperature, pH, ionic strength of the composition, or combinations of these parameters.

The mechanism of environment responsive gel formation according to the invention has not been observed or described previously. The inventive polymer $A(B)_n$ undergoes gel formation under specific environmental conditions as a result of environment-sensitive aggregation of the arms (B) of the copolymer. The aggregates of arms (B) thus form physical crosslinks between the core component (A) of the copolymers to create the gel structure when the environmental conditions are those under which the arm component (B) is insoluble. The copolymer composition readily converts between a liquid state (when solubilized either in aqueous or non-aqueous solvents) and a gel state when subjected to changes in the environmental conditions.

Figure 1:
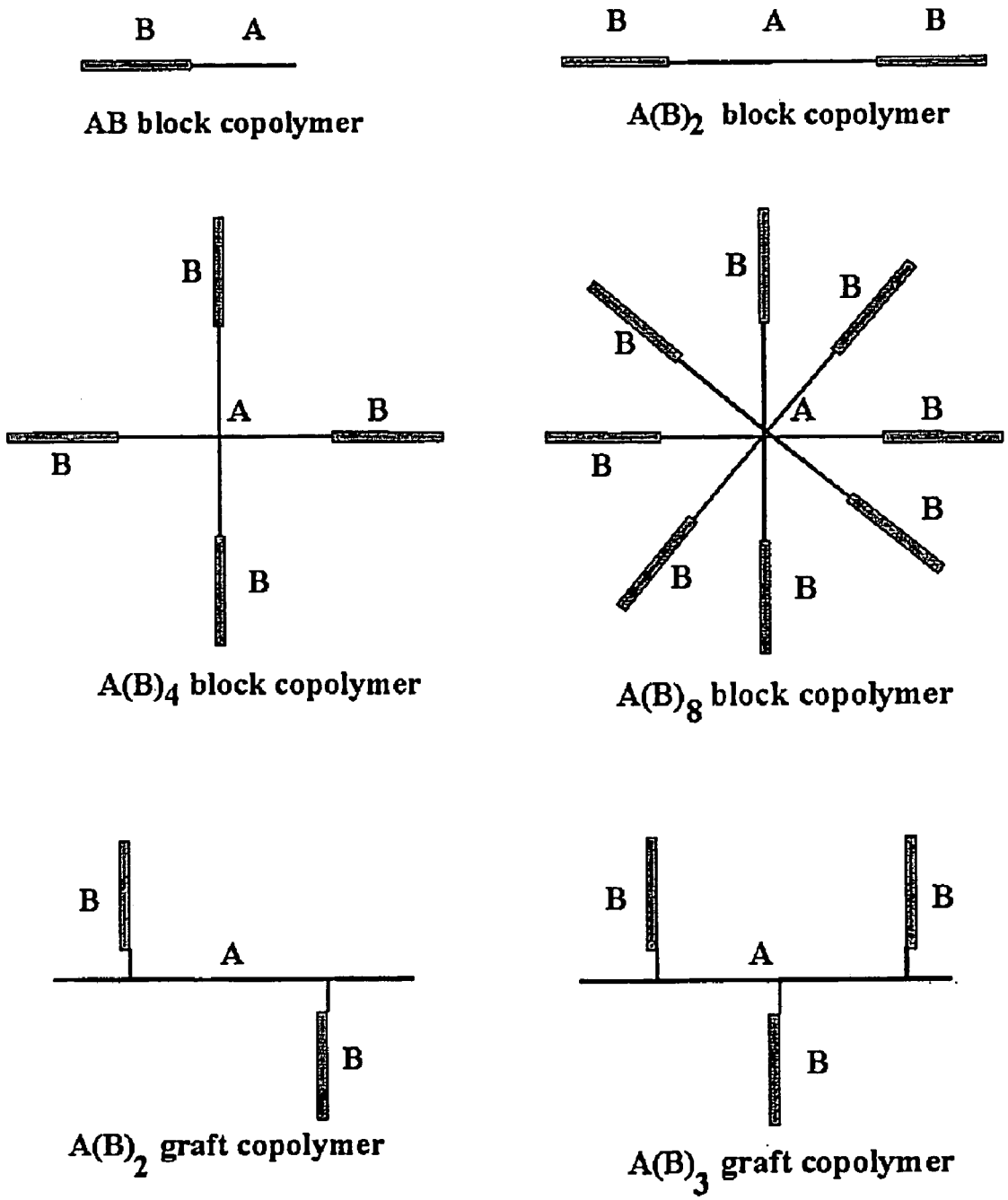
FIG. 1 is a schematic diagram of block copolymer architectures $A(B)_2$, $A(B)_4$ aid $A(B)_8$, and graft copolymer architectures $A(B)_2$ and $A(B)_3$, according to the invention, shown here for comparison purposes with polymer AB.

According to one embodiment, the inventive copolymer readily dissolves in water at room temperature to form a low viscosity solution, but becomes a gel at a temperature just below body temperature. The copolymer contains an unresponsive core (A) to which a varying number of environment-responsive arms (B) are attached. Thus, the copolymer has a general structure A(B)n. The arms (B) can be attached at any point along the core (A), provided the arms are accessible to the arms of other molecules for intermolecular aggregation upon changes in environmental conditions. For example, the arms may be attached to the ends of the core, thus forming a block copolymer, or may be attached along the chain of the core, thus forming a graft copolymer. FIG. 1 diagrammatically illustrates two-arm, four-arm and eight-arm block copolymer structures $A(B)_2$, $A(B)_4$ and $A(B)_8$, and graft copolymer structures $A(B)_2$, $A(B)_3$, with comparison to structure AB.

The core (A) may be a homopolymer or a copolymer, either linear or branched, and is chosen so that the core (A) itself is soluble in the selected solvent over the range of environmental conditions of interest. The arms (B) are chosen such that B itself would switch between being soluble and insoluble in the selected solvent between the environmental conditions of interest. When the core and arms are incorporated into a copolymer of structure A(B)n, the copolymer is soluble in the selected solvent in conditions under which the arms are soluble. However, when an environmental condition is changed to a condition under which the arms (B) themselves would be insoluble, the B component of the copolymer precipitates to form aggregated domains with B components of adjacent copolymers. The aggregated B components are linked by A segments since B and A components are covalently linked within a copolymer molecule. Thus, a three dimensional gel structure is formed containing many A segments connected via physical crosslinks of B aggregated domains.

In the resulting gel, the inventive copolymer incorporates an equilibrium quantity of solvent due to the compatibility between core A and the solvent, thereby forming a solvent-containing gel.

According to one embodiment of the invention, PEG is used as core A, poly(N-isopropyl acrylamide) (PNIPAAm), a temperature responsive polymer, is used for arms B. Copolymers are formed with varying numbers of PNIPAAm arms. These copolymers are water soluble at room temperature, forming low viscosity liquid aqueous solutions. However, upon heating, the copolymers rapidly and reversibly form strong gels (in less than a minute), exhibiting little syneresis.

The gelable composition according to the invention may contain mixtures of A(B)n copolymers that contain different A components, different B components, or have different n, or any combination thereof. In this way, mixtures can be used to optimize gelation kinetics or to achieve gel properties desirable for a particular application.

The Core. The core (A) is chosen such that, on its own, the core (A) is soluble in the selected solvent over the range of environmental conditions of interest. Thus, the core may be selected from homopolymers, or the core may itself be a copolymer (random, block or graft), either linear or branched, provided that A is soluble over the range of environmental conditions of interest.

Core (A) may either be provided as a stable compound or as a degradable compound. In the case where the core is degradable, the copolymer or copolymer composition degrades over time under appropriate conditions. For example, if the core is biodegradable in a physiological system, eventually the polymer structure will break down, resulting in release of the arms, and ultimately removal of the copolymer structure from the physiological system.

A number of possible cores (A) can be used according to the invention. The core may be selected from any synthetic, natural or biological polymers, including but not limited to polyethylene glycol (PEG) of varying molecular weights and degrees of branching, polyvinyl pyrrolidone, polyvinyl alcohol, polyhydroxyethylmethacrylate, and hyaluronic acid. Optionally, the core can have reactive groups at a variety of positions along or within its structure.

The Arms. The arms (B) are chosen such that B itself converts between being soluble and insoluble in the selected solvent when exposed to the environmental condition of interest.

The arms B may be selected according to an environment responsiveness suited to the intended application of the invention. For example, for in situ clinical applications, water-solubility under ambient conditions and aggregation under physiologic conditions is a desirable property of B. The environmental condition triggering the switch between ambient and physiological conditions may be selected from, but is not limited to, temperature, pH, ionic strength, and combinations thereof.

A number of choices for the arms (B) of the copolymer exist, including, but not limited to poly-N-isopropyl acrylamide (PNIPAAm), which is a temperature responsive polymer, hydroxypropylmethyl cellulose and other methyl cellulose derivatives, poly(ethylene glycol vinyl ether-co-butyl vinyl ether), polymers of N-alky acrylamide derivatives, poly(amino acid)s or peptide sequences such as silk and elastin peptides, poly(methacryloy L-alanine methyl ester), poly(methacryloy L-alanine ethyl ester). Nitrocellulose may be used as arms (B), for example when ethanol is used as solvent. Nitrocellulose in ethanol is known to form gel upon warming (Newman et al., J. Phys. Chem. 60:648–656, 1955).

Arms (B) may be formed from a copolymer, for example a copolymer of vinyl ether of ethylene glycol and butyl vinyl ether, which may be used in an aqueous solvent system. For a copolymer, the LCST beyond which a polymer changes solubility, depends on the mole ratio of the constituent components. In the examples given by Kudaibergenov et al. (Macromol. Rapid. Commun, 16: 855–860, 1995), the LCST values range from 20° C. to 90° C. over a mole ratio range of 72:28 to 95:5.

Arms (B) may be formed from poly(methacryloyl-DL-alanine methyl ester) or derivatives thereof. In the paper by Ding et al. (Radiat. Phys. Chem., 42 (4–6): 959–962, 1993), the LCST of the examples given are between 20° C. to 40° C. The gel swells at low temperature (i.e., 0° C.) and starts to de-swell upon warming to 20° C. or above.

Further, the arms (B) may be formed of methyl cellulose or derivatives thereof. Depending on specifics of the chemical composition, especially the degree of methylation, methyl cellulose and its derivatives were report to have a LCST in the range of 40° C. to 70° C. (Nishimura et al., Macromol. Symp., 120: 303–313, 1997).

The arms (B) may be attached to the unresponsive core (A) at any location on the core, as long as the arms remain accessible to the arms of adjacent copolymer molecules, as part of the inventive composition. This structure allows for intermolecular aggregation of arms (B) when the environmental condition is altered such that B itself would become insoluble in the selected solvent. For example, arms B may be positioned at the ends of the core, thus forming a block copolymer, or along the chain of the core thus forming graft copolymers.

As used herein, the structure "A(B)n" denotes a copolymer having arms (B) positioned on the core (A) in any manner, so as to form a block or graft copolymer. Arms (B) may be located at one or more ends of A, forming a block or star copolymer configuration, or may be located along the length of the core, thereby forming a graft copolymer, with B positioned as "brushes" along the core, or may be positioned randomly along the core, provided the arms are accessible for aggregation with the arms of adjacent molecules.

Further, as the structure "A(B)n" is understood to mean that A and B are present in the specified ratio within a given molecule, but that the covalent bond between A and B may also comprise an additional component, resulting in A and B being covalently linked through such an additional component. An example wherein the additional component is a reactive spacer is described in more detail below.

The number of arms (B) attached to the core (A) is selected such that n of A(B)n is a number which is larger than, but not equal to one. For any given copolymer molecule, n is an integer greater than 1. Thus, the ratio of arms to core in the architecture of any given copolymer molecule is 2:1, (n=2) or greater. For example, the ratio of arms to core can be 4:1 (n=4) or 8:1 (n=8). The number of arms is not limited, provided that core is of adequate size to accommodate the selected number of arms, while still allowing the arms of one copolymer molecule to access the arms of an adjacent copolymer molecule when in solution. The selection of the number of arms may also depend on the desired properties of the gel, for example, to achieve a stronger or weaker gel, the number of arms may be adjusted.

The gelable composition formed according to the invention may be comprised of a plurality of different copolymers. Taking into account the proportions of different copolymer architectures within the composition, an average A(B)n can be determined for the composition. In this case, the average n ($n_{avg}$) must be greater than 1, but non-integer values of $n_{avg}$ are possible for any particular gelable composition. For example if the composition contains a mixture of copolymers of varying architectures, such as 50% copolymer AB and 50% copolymer A(B)$_2$, the $n_{avg}$ of the composition is 1.5. In the inventive composition, $n_{avg}>1$, taking into account all forms of A(B)n copolymers in the composition. For any individual copolymer molecule within the composition, n is an integer number, as described above. In compositions which contain a mixture of copolymers, it is possible to have a gel-forming composition comprising some copolymer molecules with n=1, some with n=4, etc. In order for such a composition to be gelable according to the invention, $n_{avg}$ should be adequately greater than 1, so that enough copolymer molecules with n>1 are present in the composition to allow formation of the gel network. In this way, copolymer molecules having the structure AB (n=1), which would not ordinarily form a gel with other AB copolymers, can become part of the gel network by having their single arm segment incorporated into the aggregates formed by the molecules having n>1.

Reactive Spacers. Reactive spacers "C" may be present between core A and arms B, thereby forming a copolymer of the generic structure A(CB)n. It is understood that A(CB)n is a variant or embodiment of A(B)n, as the structure A(B)n is understood to mean that A and B must be present in the specified ratio, but that the covalent bond between A and B may also comprise an additional component, resulting in A and B being covalently linked through component C.

Figure 2:
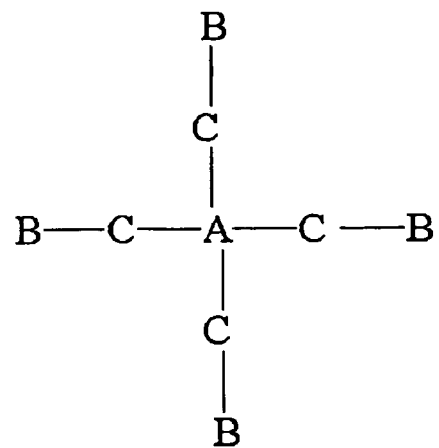
FIG. 2 is a schematic diagram of copolymer architectures $A(CB)_2$ and $A(CB)_4$ according to the invention.

FIG. 2 illustrates two-arm and four-arm copolymer structures with reactive spacers C. As can be seen in FIG. 2, when a reactive spacer C is present between A and B, the basic structure of A(B)n is met, and merely includes an additional component C within the covalent bonds binding A to B. In the embodiment of A(CB)n, two covalent bonds bind A to B, specifically, the bond between A and C, and the bond between C and B.

Reactive spacers C may be incorporated to allow cleavage of the copolymer, for such purposes as for rendering the copolymer degradable under desired conditions. Reactive spacer C may degrade via any suitable reaction, including but not limited to chemical reactions, biochemical reactions, enzymatic degradation, or photo-induced reactions. In the case where a reaction of the reactive spacers results in cleavage of the copolymer, as C degrades, A(CB)n is split into individual A and B components. In the context of a physiological application, if core A and arms B are of low enough molecular weight, they can be cleared from the site and removed from the body via renal clearance.

Biologically Active Molecules. A biologically active molecule may be included in the invention either through covalent attachment of the molecule to the structure of the copolymer or by including the molecule in a copolymer composition. In the case where the biologically active molecule is included in the copolymer composition, but not incorporated into the copolymer itself, the biologically active molecule is optimally selected from those having some degree of solubility in the desired solvent.

According to an embodiment wherein the biologically active molecule D is attached to the copolymer, it may be bound to either the core (A) or the arms (B) in such a way that the attachment allows release of the biologically active molecule D from the copolymer. For example, a covalent attachment of D to A may occur via a degradable spacer, such as C, described above.

As with the introduction of reactive spacer (C) in the copolymer, introduction of biologically active molecule D, with or without spacer C, is considered an embodiment of A(B)n. It is understood that D may be covalently attached to either A or B, and a copolymer polymer so formed would meet the requirement structure of A(B)n. The structure A(B)n is understood to mean that A and B must be present in the specified ratio, but that the covalent bond between A and B may also comprise an additional component such as D, through which the covalent attachment of A and B, may be indirectly achieved.

According to a further embodiment of the invention, biologically active components may be included in the polymeric composition formed according to the invention, but without any covalent link to the polymer itself. Advantageously, when a gel is formed, a biologically active compound present in the polymeric solution becomes trapped in the gel structure. This arrangement is conducive to slow release of the biologically active molecule from the gel structure within a physiological environment.

A biologically active molecule for incorporation into the copolymer or copolymer composition may be any which causes a physiological change or effect, such as a low molecular weight compound, drug, antibody, growth factor, peptide, oligonucleotide, genetic sequence, or compounds that modulate cell behaviours such as adhesion, proliferation or metabolism. A biologically active molecule may be attached to the copolymer or included in the copolymer composition in order to promote the viability or proliferation of cells encapsulated in such gels, or to influence the production of compounds by such cells.

The Solvent. Various solvents may be used with the copolymer composition. The solvent may be aqueous, including water, sodium chloride solutions such as physiological saline, cell culture media, or any medium that approximates a biological system, such as extracellular matrix. The pH, and tonicity of a solvent may be any which allows adjustment as appropriate, so that the environmental condition can be adjusted within the copolymer composition in order for the composition to take on a gel form. Non-aqueous solvents may be used, or combination solvents including a polar organic and an aqueous component. For example, an alcohol may be used as the solvent, with or without water. Ethanol, methanol, isopropyl alcohol and other alcohols may be used as a solvent. Other polar organic solvents may be used alone or in combination with water. Non-polar organic solvents may be used with appropriate copolymers, such that A is soluble in the solvent, and B is soluble under certain environmental conditions and insoluble under other environmental conditions.

The term "solvent" may also refer to any prepared mixture of components which may include proteins, growth factors, buffers, ions, and other co-solutes. For example, culture media and extra cellular solutions contain water in combination with a number of co-solutes which are considered part of the solvent. Further, other soluble components, such as polymers may be included in the solvent. Such polymers may, for example, be synthetic polymers or copolymers that do not aggregate with the copolymer having A(B)n architecture. The solvent may contain, for example, the polymer used as core component (A) in the copolymer A(B)n. When such a polymer or copolymer is included in the solvent, it would not be considered in the calculation of $n_{avg}$ unless it had a structure A(B)n and was capable of aggregation with arms B of the inventive copolymer. As an example of solvents which include polymers, PEG homopolymer and others may be included in the solvent.

Regardless of the solvent selected for use with the invention, the core (A) is selected to be soluble in the solvent over a range of environmental conditions of interest. The arms (B) are environment-responsive components which are soluble in the solvent under one set of environmental conditions, and which become insoluble in the solvent under different environmental conditions of interest.

Within the composition, the copolymer can be present in the solvent at any concentration that allows gelation to occur, for example a level of from about 5% to about 50% by weight, or from about 10% to about 25% by weight. This concentration depends on the nature of the solvent and the copolymer.

Applications of the Invention. The invention may be used for either physiological or industrial applications. Physiological and clinical applications of the invention include, but are not limited to, delivery of biologically active molecules, tissue and biomedical engineering, and therapeutics. Industrial applications of the invention include but are not limited to synthetic processes requiring timed release of reactive components, or as barriers.

The invention can be applied to delivery of biologically active molecules, for example but not limited to in vitro formation of drug delivery systems, in situ drug delivery, in situ gene delivery. The inventive polymer may be used to form drug delivery systems in vitro, which could then be implanted into a physiological region of a subject. Drug delivery systems may be formed in situ by suspending drug-containing particles in the copolymer composition, then injecting the composition into, or applying the composition onto specified sites of a subject causing gel formation to occur in vivo. Genes may be delivered in vivo using the inventive polymers and compositions. Gene delivery systems in situ can be formed by suspending gene-containing vesicles in the polymer solutions, then injecting the solutions into, or applying the solutions onto specified sites of patients causing gel formation to occur in vivo. Possible sites for implantation for in vitro formed systems or for insertion of in situ forming systems of biologically active molecules include but are not limited to periodontal cavities, intramuscular sites, subcutaneous sites, tumors, bones, joints, intraocular sites, sites that have been exposed by surgery, and wound sites.

The process for forming an in vitro implant may additionally involve maintaining the composition at least at a gelling temperature prior to insertion of said implant into a subject, so that the implant does not convert back to a liquid state.

For compositions having an LCST between ambient temperature and body temperature, the environmental condition that triggers gel formation is heating to body temperature. Thus, inserting the composition into the body causes the biologically active molecule to be trapped in the gel at the site of application, and sustained release from the site would then result.

Further, the invention may be used for in vitro or in situ encapsulation of cells. For encapsulation of cells in vitro, cells can be grown in incubation medium to which the copolymer is added when desirable, so as to keep cells in suspension under certain environmental conditions, but to retain them in a gel when environmental conditions are changed. Encapsulation of cells may also occur in situ by suspending cells in the copolymer composition under conditions at which the composition is a liquid (for example, below LCST), then injecting the composition into, or applying the composition onto specified sites of patients causing gel formation to occur in vivo. The sites for in situ injection of suspended cells in the composition, or for insertion of an in vitro formed implant of encapsulated cells can be selected from, but are not limited to, periodontal cavities, intramuscular sites, subcutaneous sites, tumors, bones, joints, intraocular sites, sites that have been exposed by surgery, and wound sites.

For applications involving encapsulated cells, the length of chain segments between the physical crosslinks of the copolymer may be selected such that the mesh size between crosslinks provides the appropriate molecular weight cut-off to provide immunoisolation of the encapsulated cells from the intended host while allowing the diffusion of desired nutrients to the cell, and the release of desired agents from the encapsulated cells to the host. In an application of in situ forming cell-containing gels, the copolymer would be soluble in water at ambient conditions (ie. room temperature), and the composition including suspended cells is injected into or applied onto a patient at the desired site. Body temperature triggers gel formation, thus causing the cells to be trapped in the gel at the site of injection or application. Cell proliferation and secretion of desired substances from the cell may then occur.

In cell-containing applications, it may be particularly advantageous to incorporate into the gel peptides or growth factors that promote cell adhesion, cell proliferation or otherwise influence cell metabolism in the desired manner. Such compounds may either be covalently linked to the copolymer, or incorporated in solid particles or liquid droplets that are co-encapsulated in the composition with the cells.

The composition may be used as a coating, barrier, sealant, filling or blocker of an anatomical structure or region, formed either in situ, or formed in vitro and implanted to an appropriate region. The composition may be positioned within a biological structure or on top of a biological structure. For example, the composition may be sprayed onto a wound site to provide a protective coating for the wound. It may also be injected into a blood vessel to block blood flow in that vessel. Such an application may be useful upstream of a tumor to block blood flow to the tumor. It may also be used as a temporary sealant during surgery.

For physiological applications of the composition according to the invention, it is advantageous that the gelation is reversible. For example, an implant placed in a subject in situ can be reversed by liquifying the implant, such as by localized cooling of the area in which the implant was applied. Applying a cold compress, ice, or using other methods of localized cooling could be used to effect liquification of the composition from a gel state.

Industrial (non-physiological) applications of the invention include separation processes, chemical synthetic processes requiring timed or environmentally cued release, or for partitioning of reactants. For example, a reactant in an aqueous reaction may be encapsulated within the composition in gel form (ie. at a temperature above LCST). When the reaction is cooled below LCST, the encapsulated reactants are released due to the phase change of the composition from gel to liquid, thereby releasing the encapsulated reactant to the reaction. Thermocycling reactions which require accurately timed additions of a reactant can incorporate the reactant in the inventive composition to ensure accurate release of a reactant at a particular temperature. In other industrial applications, the copolymer composition can provides a barrier, coating, blockage, sealing or filling. The gelation of the composition formed according to the invention is advantageously reversible over a number of cycles. This reversibility allows repeated gelation and liquification cycles.

EXAMPLES

Examples of the invention are presented below to illustrate the invention, but not to limit the scope of the invention.

Reagent Preparation and Handling. Reagents used throughout the examples are described below, along with appropriate storage requirements.

$Ce^{4+}$ Solutions (0.4 M) are prepared by directly dissolving solid ceric ammonium nitrate $Ce(NO_3)_6(NH_4)_2$ in distilled deionized water. The solution is either prepared fresh everyday, or if it is to be stored for a short duration, it is first sonicated to remove dissolved oxygen, then placed in a tightly capped high density polyethylene (HDPE) or polypropylene (PP) bottle, and stored at 5° C.

NaOH solution (1 N) is prepared from 10 N NaOH by dilution with distilled deionized water. The prepared solution is stored in a HDPE bottle.

N-isopropyl acrylamide (NIPAAm) monomer of 99% purity stabilized with 0.1% methoxyhydroquinone (MHQ), purchased from ACROS Organics, is further purified before use. The three major impurities are acrylamide monomer, MHQ and acrylic acid. They are removed by recrystalization followed by ion-exchange processes. NIPAAm monomer is first dissolved in 50/50 heptane/toluene solvent at 60° C. slightly above the melting point of NIPAAm. The warm solution is filtered through 0.8 μm nylon membrane to eliminate undissolved impurities. The warm aliquot is then put into an ice bath to recrystalize NIPAAm monomer. The NIPAAm crystal is recovered by vacuum filtration. The recrystalization process is repeated twice to eliminate MHQ and residual acrylamide monomers. The solid is then dissolved in distilled deionized water as a 20 wt % solution. The solution is poured into a bed of anionic exchange resin (IRA-402, $Cl^-$ form, SUPELCO) to eliminate trace amount of acrylic acid. The anion-free NIPAAm solution is separated from the resin by vacuum suction. The high purity NIPAAm monomer is then recovered by freeze-drying at −55° C., and under a vacuum below $10^{-4}$ bar.

OH-terminated PEG is selected and obtained as follows. Polyethylene glycol of various architectures and with varying number of chain ends terminated by reactive hydroxyl groups are purchased from Shearwater Polymers, Inc. They are used without further purification or modification.

The composition of the standard extracellular solution (formulated for beta-cell lines) was as follows: NaCl (140 mM), KCl (4 MM), $MgCl_2$ (1 mM), $CaCl_2$ (2 mM), and HEPES (10 mM). The final pH of 7.3 was achieved by adjusting with NaOH.

F-12K Nutrient Mixture (Kaighn's Modification) made by GibcoBRL was used as the cell culture media referred to herein as F-12K. Purified collagen used in any methods herein was Vitrogen™, obtained from Cohesion Technologies Inc., Palo Alto, Calif.

Example 1

Two-Armed Block Copolymer PNIPAAm-PEG-PNIPAAm

Linear polyethylene glycol (MW 5077) with terminal hydroxyl groups at both ends of the chain, $HO(CH_2CH_2O)_{113}H$, was purchased from Shearwater Polymer (product name Sunbright DKH-50H, Lot. 68559) and used without further treatment. This reagent is herein referred to as the two-armed PEG.

The two-armed PEG (1.0 g) was mixed with 1.35 g of purified NIPAAm, dissolved in water, then mixed with 2.0 ml of a 0.4 M $Ce^{4+}$ solution, and 0.8 ml of 1N NaOH solution. The total mixture was 15 ml in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a helium blanket. The reaction vial was made of polypropylene instead of glass to avoid $Ce^{4+}$/OH-glass side reaction, which could lead to an increased production of PNIPAAm homopolymer. The product of this reaction is predominantly a tri-block copolymer consisting of a central segment of PEG, with two separate segments of PNIPAAm covalently attached to either end of the PEG segment.

The unreacted NIPAAm, PEG and residual Ceric salts, and PNIPAAm homopolymer were removed by dialysis using an ester cellulose membrane (Fisher Scientific) in a water bath for four weeks. The water was changed every 24 hours. The copolymer was recovered from the solution by high vacuum freeze-drying at −55° C.

A 10 wt % sample was prepared by dissolving one gram of the tri-block polymer in 9.0 ml of cold water at 5° C. Below 30° C., the solution was colorless and transparent. Between 5° C. to 25° C., the solution was low in viscosity and thus could be easily drawn into a syringe through a 25 gauge needle. Upon heating to above 32° C., the solution became opaque immediately, and the entire 10 mL solution turned into a solid white gel in less than two minutes. The gel occupied the entire solution volume. The gel showed some elasticity, and could hold its own shape even when the sample vial was inverted. Storage at 37° C. resulted in slight shrinkage of the gel (10% in 24 hours, 20% in two months). Differential scanning calorimetry measurements of the sample showed an endothermic first order transition temperature at 33.1° C. The width at half peak height was 2.2° C. The phase transition observed was completely reversible over many cycles.

Example 2

Four Armed Block Copolymer PEG-(PNIPAAm)$_4$

Four-arm branched polyethylene glycol (MW 10486) with one terminal hydroxyl group at each branch was purchased from Shearwater Polymer (product name Sunbright PTE-10000, Lot. 76606) and used without further treatment. This reagent is herein referred to as the 4-armed PEG.

The four-armed PEG (1.0 g) was mixed with 1.35 g of purified NIPAAm, dissolved in water, then mixed with 2.0 ml of a 0.4 M Ce$^{4+}$ solution, and 0.8 ml of 1N NaOH solution. The total mixture was 15 mL in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a helium blanket. The reaction vial was made of polypropylene instead of glass to avoid Ce$^{4+}$/OH-glass side reaction, which could lead to an increased production of PNIPAAm homopolymer. The product of this reaction is predominantly a branched copolymer consisting of a central four-armed PEG, and individual PNIPAAm segments covalently attached to the end of each arm of the four-armed PEG.

The unreacted NIPAAm, PEG and residual Ceric salt, and PNIPAAm homopolymer were removed by dialysis using an ester cellulose membrane [Fisher Scientific] in a water bath for four weeks. The water was changed every 24 hours. The copolymer is recovered from the solution by high vacuum freeze-drying at −55° C.

A 10% wt sample was prepared by dissolving one gram of the four-armed copolymer in 9.0 ml of 5° C. cold water. Below 30° C., the solution was colorless and transparent. Between 5° C. to 25° C., the solution was low in viscosity and thus could be easily drawn into syringe through a 25 gauge needle. Upon heating to above 32° C., the solution became opaque immediately, and the entire 10 mL solution quickly turned into a solid white gel in less than two minutes. The gel occupied the entire solution volume. The gel showed some elasticity. It could hold its own shape even when the sample vial was inverted. The gel was cohesively strong enough to be picked up by a pair of tweezers, and was stronger than the gel formed according to Example 1. Storage at 37° C. resulted in negligible shrinkage (less than 5% in two months). Differential scanning calorimetry measurements of the sample showed an endothermic first order transition temperature at 32.6° C. The width at half peak height was 3.4° C. The phase transition observed was completely reversible over many cycles.

Example 3

Eight Armed Block Copolymer PEG-(PNIPAAm)$_8$

Eight-arm branched polyethylene glycol (MW 19770) with a terminal hydroxyl group at each branch was purchased from Shearwater Polymer (product name Sunbright HGEO-20000, Lot. 7D543) and used without further treatment. This reagent is herein referred to as the 8-armed PEG.

The eight-armed PEG (1.0 g) was mixed with 1.35 g of purified NIPAAm, dissolved in water, then mixed with 2.0 ml of a 0.4 M Ce$^{4+}$ solution, and 0.8 ml of 1N NaOH solution. The total mixture was 15 mL in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a Helium blanket. The reaction vial was made of polypropylene instead of glass to avoid Ce$^{4+}$/OH-glass side reaction, which can lead to an increased production of PNIPAAm homopolymer. The product of this reaction is predominantly a branched copolymer consisting of a central block of the eight-armed PEG, and eight separate segments of PNIPAAm covalently attached to the end of each arm of the eight-armed PEG.

The unreacted NIPAAm, PEG and residual Ceric salt, and PNIPAAm homopolymer were removed by dialysis using ester cellulose membrane [Fisher Scientific] in a water bath for four weeks. The water was changed every 24 hours. The copolymer is recovered from the solution by high vacuum freeze-drying at −55° C.

A 10 wt % sample was prepared by dissolved one gram of the eight-armed copolymer product in 9.0 ml of cold water at 5° C. Below 30° C., the solution was colorless and transparent. Between 5° C. to 25° C., the solution was low in viscosity and thus could be easily drawn into syringe through a 25 gauge needle. Upon heating above 32° C., the solution became opaque immediately, and the entire 10 mL solution quickly turned into a solid white gel in less than two minutes. The gel occupied the entire solution volume. The gel showed some elasticity. It could hold its own shape even when the sample vial was inverted. The gel was cohesively strong enough to be picked up by a pair of tweezers, and was stronger than the gel formed according to Example 1, and comparable in strength to the gel of Example 2. Storage at 37° C. resulted in negligible gel shrinkage (less than 5% in two months). Differential scanning calorimetry measurements of the sample showed an endothermic first order transition temperature at 33.5° C. The width at half peak height was 2.8° C. The phase transition observed was completely reversible over many cycles.

Example 4

Synthesis, Purification and Thermal Characteristics of 50/50 Copolymers of PEG/PNIPAAm having Architecture A(B)$_2$, A(B)$_4$ and A(B)$_8$ The copolymers were synthesized by Ce$^{4+}$/OH redox initiated free radical polymerization in water. Four hydroxyl-terminated PEGs were purchased from Shearwater and used without further purification: monomethoxy-PEG of 2,000 Da (i.e., 1 arm of length 2,000 Da), linear PEG diol of 4,600 Da (i.e., 2 arm PEG with each arm length of 2,300 Da), 4 arm star PEG of 9,300 Da (arm length=2,325 Da), and 8 arm star PEG of 19,700 Da (arm length=2,460 Da). All functionalized PEGs have polydispersity indices of less than 1.04.

The following exemplary conditions and procedure may be used for batch synthesis of PEG-PNIPAAm copolymers having architecture A(B)$_2$, A(B)$_4$ and A(B)$_8$, shown for comparison purposes with AB. The reaction solution volume is 30 ml in all cases. No NaOH is added to the reaction solution. The solvent is distilled water, and the reaction temperature is 30° C. The reagents are cold mixed at 5° C., and then sonicated for 10 to 20 minutes to eliminate dissolved oxygen. Subsequently, the mixture is subjected to an inert gas surge for 5 minutes to pre-saturate the solution with Helium gas. The reaction is then allowed to proceed for 24 hours under a water-saturated Helium blanket. The reaction vessel is made of Teflon (or polypropylene) instead of glass to avoid Ce$^{4+}$/OH-glass side reaction, which could lead to an increased production of homopolymer. At the end of 24 hours, the mixture was diluted to 100 ml by adding cold distilled water and placed in a 5° C. refrigerator to quench the reaction. The detailed reaction conditions are summarized in Table 1.

The copolymers were purified by dialysis. Cellulose ester membrane of various molecular weight cut-off [Fisher Scientific] were selected for such purpose. The details of purification conditions are provided in Table 2, including the molecular weight cut off (MWCO) of dialysis tubes used, and the recovered yield calculated as (dry copolymer)/(initial PEG mass+initial monomer mass).

TABLE 2

Conditions for Purification of 50/50 PEG/PNIPAAm Copolymers

| Copolymers | MWCO of Tube | Dialysis Time | Recovered Yield (wt %) |
|---|---|---|---|
| AB | 3,500 | 4 weeks | 15~25% |
| A(B)$_2$ | 8,000 | 4 weeks | 20~30% |
| A(B)$_4$ | 15,000 | 4 weeks | 20~30% |
| A(B)$_8$ | 25,000 | 4 weeks | 15~25% |

The copolymer molecular weights were determined by proton NMR [Varian Unity Plus 500 MHz]. The ratio of the methyl protons in isopropyl groups to the methylene protons of PEGs was used to determine the ratio of NIPAAm to ethylene glycol repeat units. Using the known molecular weight of PEG, the molecular weight of PNIPAAm segments, and thus the copolymer molecular weight can be deduced. The composition and characteristics of copolymers formed are given in Table 3.

TABLE 1

Conditions for Batch Synthesis of 50/50 PEG/PNIPAAm Copolymers

| Structure | Reaction Temp. (° C.) | Reaction volume (ml) | Reaction Duration (hr) | 0.4 M Ce$^{4+}$ vol. (ml) | NIPAAm mass (g) | PEG mass (g) | PEG/NIPAAm feed ratio | PEG/PNIPAAm final composition |
|---|---|---|---|---|---|---|---|---|
| AB | 30 | 30 | 24 | 8.0 | 1.0 | 3.0 | 75/25 | 49/51 |
| A(B)$_2$ | 30 | 30 | 24 | 8.0 | 0.81 | 1.5 | 65/35 | 48/52 |
| A(B)$_4$ | 30 | 30 | 24 | 8.0 | 0.87 | 1.2 | 58/42 | 51/49 |
| A(B)$_8$ | 30 | 30 | 24 | 8.0 | 0.79 | 1.0 | 56/44 | 49/51 |

TABLE 3

Composition and Characteristics of Copolymers

| Structure | "A" Block Weight[a] (Da) | PEG MW per Arm (Da) | "B" Block Weight (Da)[b,c] | PEG/PNIPAAm (by weight) | Total Molecular Weight (Da)[c] |
|---|---|---|---|---|---|
| AB | 2,000 | 2,000 | 2,100 ± 200 | 49/51 | 4,100 ± 200 |
| A(B)$_2$ | 4,600 | 2,300 | 2,500 ± 200 | 48/52 | 9,600 ± 400 |
| A(B)$_4$ | 9,300 | 2,330 | 2,200 ± 200 | 51/49 | 18,200 ± 800 |
| A(B)$_8$ | 19,700 | 2,460 | 2,600 ± 200 | 49/51 | 40,000 ± 1,600 |

[a]As reported by manufacturer; polydispersity of 1.04 or better.
[b]Average from three synthesis batches
[c]As calculated from NMR analysis The thermal characteristics of the copolymers were determined by differential scanning calorimetry (DSC) [TA2010, TA Instrument]. DSC scans of aqueous solutions of each copolymer at various concentrations were taken at a heating rate of 2° C./minute. Transition temperatures, both onset of thermal transitions ($T_{onset}$) and peak temperature of endotherm ($T_{max}$), and the enthalpy of thermal transition normalized to PNIPAAm content, ΔH (J/g of PNIPAAm, were determined. The results are tabulated in Tables 4 to 7 for copolymers, and in Table 8 for solutions of PNIPAAm homopolymer (comparative example) in water. The measurement precision for temperature is ±0.2° C. and enthalpy is ±2 J/g for all cases.

TABLE 4

DSC Results for 1 arm 50/50 PEG/PNIPAAm Copolymer AB (Comparative Example)

| Concentration | $T_{onset}$ (° C.) | $T_{max}$ (° C.) | ΔH (J/g of PNIPAAm) |
|---|---|---|---|
| 20% | 27.3 | 28.7 | 30 |
| 15% | 28.7 | 29.8 | 32 |
| 10% | 30.0 | 31.0 | 35 |

TABLE 5

DSC Results for 2 arm 50/50 PEG/PNIPAAm Copolymer A(B)$_2$

| Concentration | $T_{onset}$ (° C.) | $T_{max}$ (° C.) | ΔH (J/g of PNIPAAm) |
|---|---|---|---|
| 20% | 26.4 | 28.5 | 29 |
| 15% | 28.6 | 30.0 | 36 |
| 10% | 30.0 | 31.0 | 38 |

TABLE 6

DSC Results for 4 arm 50/50 PEG/PNIPAAm Copolymer A(B)$_4$

| Concentration | $T_{onset}$ (° C.) | $T_{max}$ (° C.) | ΔH (J/g of PNIPAAm) |
|---|---|---|---|
| 20% | 26.2 | 29.3 | 29 |
| 15% | 29.4 | 30.9 | 34 |
| 10% | 30.2 | 31.4 | 37 |

TABLE 7

DSC Results for 8 arm 50/50 PEG/PNIPAAm Copolymer A(B)$_8$

| Concentration | $T_{onset}$ | $T_{max}$ | ΔH (J/g of PNIPAAm) |
|---|---|---|---|
| 20% | 28.2 | 30.3 | 28 |
| 15% | 29.7 | 31.1 | 33 |
| 10% | 30.8 | 32.0 | 34 |

TABLE 8

DSC Results for PNIPAAm homopolymer (Comparative Example)

| Concentration | $T_{onset}$ (° C.) | $T_{max}$ (° C.) | ΔH (J/g of PNIPAAm) |
|---|---|---|---|
| 10% | 32.6 | 33.6 | 43 |
| 7.5% | 32.8 | 33.7 | 44 |
| 5% | 32.7 | 33.4 | 45 |

The results show that the transition temperature is concentration dependent. As concentration decreases, the transition temperature rises slightly. The range of onset temperature is between 26° C. to 31° C. for all four types of copolymers, which is a suitable range for a physiological application requiring a liquid state at an ambient temperature and a gel state at a physiological temperature. The range of ΔH values illustrates that the copolymer molecular architecture influences the phase transition of the PNIPAAm segments, while the comparison between the copolymers and the homopolymer suggests that the presence of PEG may have prevented PNIPAAm segments from fully collapsing. The enthalpy of gelation for copolymers according to the invention are about 15% to 35% lower than that of PNIPAAm homopolymer (see Table 8) measured at the equal PNIPAAm content.

Example 5

Rheological Properties and Gelation Mechanism of Block and Star Copolymers of PEG and PNIPAAM of Varying Architectures Block or star copolymers with a central hydrophilic polyethylene glycol (PEG) segment as core (A), and temperature responsive poly(N-isopropylacrylamide) (PNIPAAm) terminal segments as arms (B) of various architectures A(B)$_2$, A(B)$_4$ and A(B)$_8$, were synthesized to investigate the structures and properties relationship. A comparative copolymer having the structure AB is also evaluated. The synthesis and purification of copolymers were conducted according to the schemes given in Example 4. The compositions of the copolymers are identical to those given in Example 4 (see Table 3, Composition and Characteristics of Copolymers). All four copolymers evaluated herein are of approximately 50/50 PEG/PNIPAAm ratio by weight.

At 5° C., the viscosities of 20% wt solutions were between 700 to 950 cP, and they could be easily injected through a 25 G needle. Upon warming to body temperature, A(B)$_2$, A(B)$_4$ and A(B)$_8$ formed a strong associative network gel with aggregates of PNIPAAm segments acting as physical crosslinks, whereas AB formed a weaker gel by micellar packing and entanglement. The values of elastic modulus, loss tangent, and yield strength were between 1300 to 2600 Pa, 0.4 to 0.6, and 300 to 1000 Pa, respectively.

The mechanical and rheological properties of the copolymers were characterized using a temperature controlled rheometer [Carri-Med, TA Instrument] with a cone and plate (4 cm diameter, 2 degree angle) geometry. Yield stress ($\sigma_c$), critical strain ($\gamma_c$), and elastic and loss moduli (G', G") were determined under oscillatory mode at 37° C. Solution viscosities were measured under flow mode at 5° C. using 20 wt % copolymer solutions in water.

Figure 3:
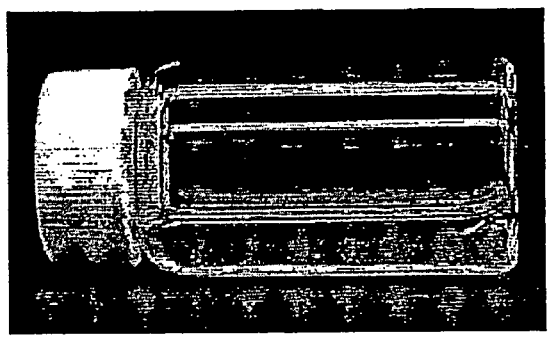
FIG. 3 illustrates an $A(B)_4$ polymer of PEG and PNIPAAm in aqueous solution. Picture A illustrates a 20% wt $A(B)_4$ solution at 25° C., while picture B illustrates a 20% wt $A(B)_4$ gel at 37° C.
Figure 3:
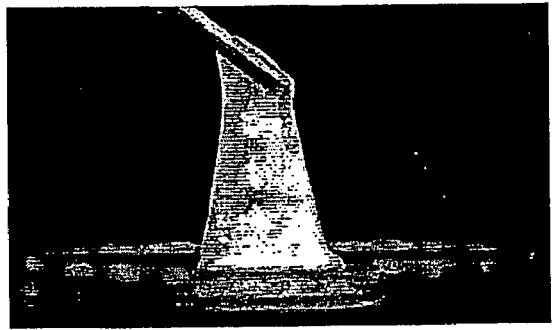

FIG. 3 illustrates a composition according to the invention comprising the A(B)$_4$ polymer of PEG and PNIPAAm in aqueous solution at a concentration of 20% by weight. As shown in picture A, the composition is a liquid at room temperature (25° C.), and forms a strong gel at body temperature (37° C.), as shown in picture B.

Figure 4:
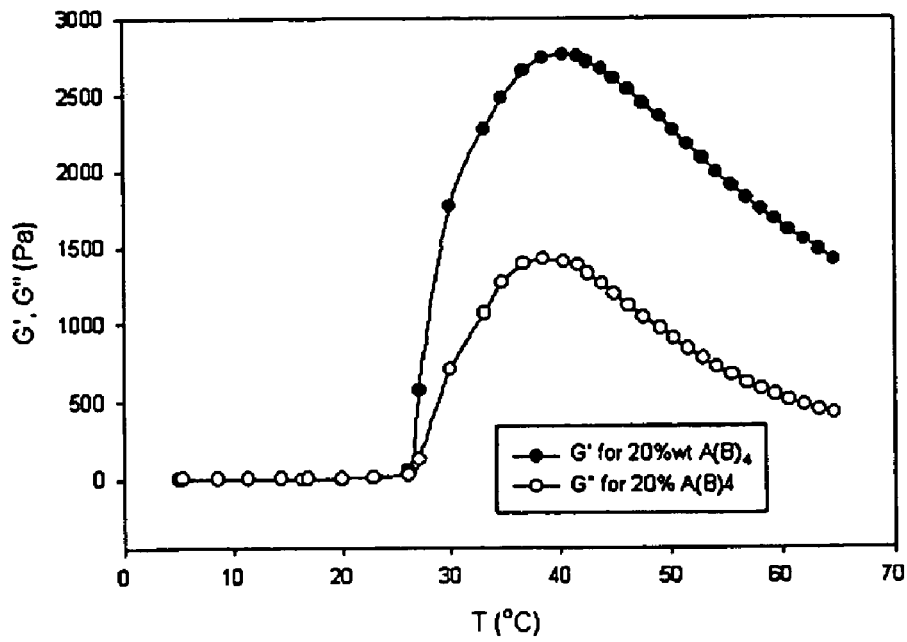
FIG. 4 illustrates that for a 20% solution of $A(B)_4$ the onset of increase in the elastic and loss moduli, shown as (A) temperature sweep of oscillatory measurement, occurs at a temperature between the onset and peak of the endotherm as detected by (B) DSC temperature scan.
Figure 4:
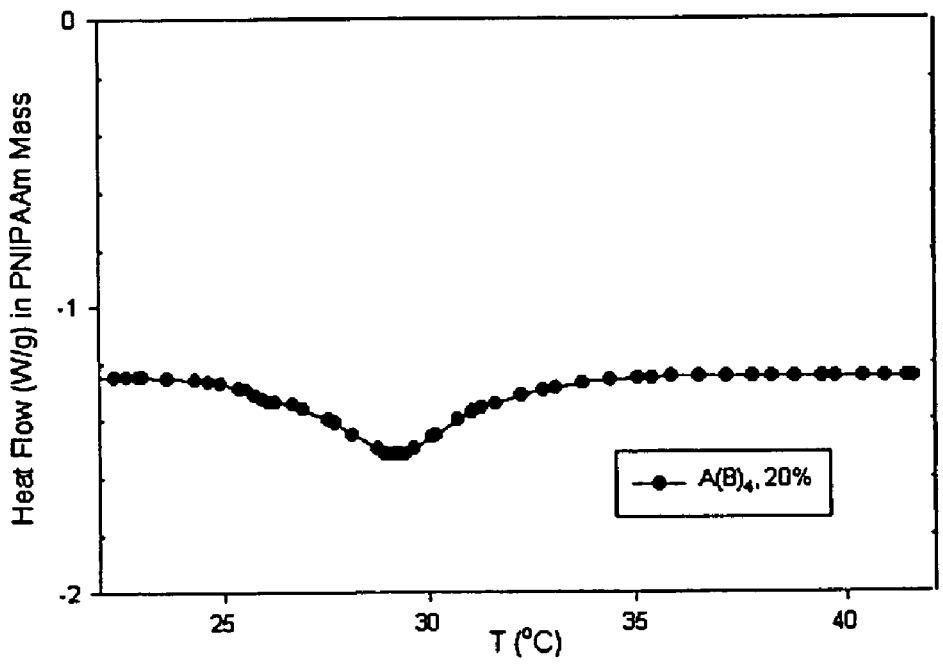

FIG. 4 illustrates that for a 20% solution of A(B)$_4$, the onset of both elastic and loss modulus, shown as (A) temperature sweep of oscillatory measurement, is between the onset and the peak temperatures in the endotherm as detected by (B) DSC temperature scan. When PNIPAAm collapses at an elevated temperature, heat is evolved, and measured by DSC. The endotherm of a DSC scan is corresponding to the molecular event of PNIPAAm segments collapsing. The synchronization of the endotherm and moduli onset temperatures illustrates that the thermal transitions are linked to the mechanical changes, and therefore the aggregation measured by the thermal transitions are at least partially intermolecular in nature. It is known that the mechanical strength (i.e., modulus) is scale to the number of crosslinks per unit volume. The higher the crosslink density, the higher the modulus will be. The inter-aggregation will lead to connection between molecules (i.e., forming physical crosslinks) which ultimately gives rise to a high mechanical strength; whereas, intra-aggregation will produce no physical crosslinks, thus no drastic rise of modulus is expected upon transition temperature. The rapid rise of modulus at the onset of endotherm illustrates a gelation mechanism of network formation for the multiple arm copolymers.

Figure 5:
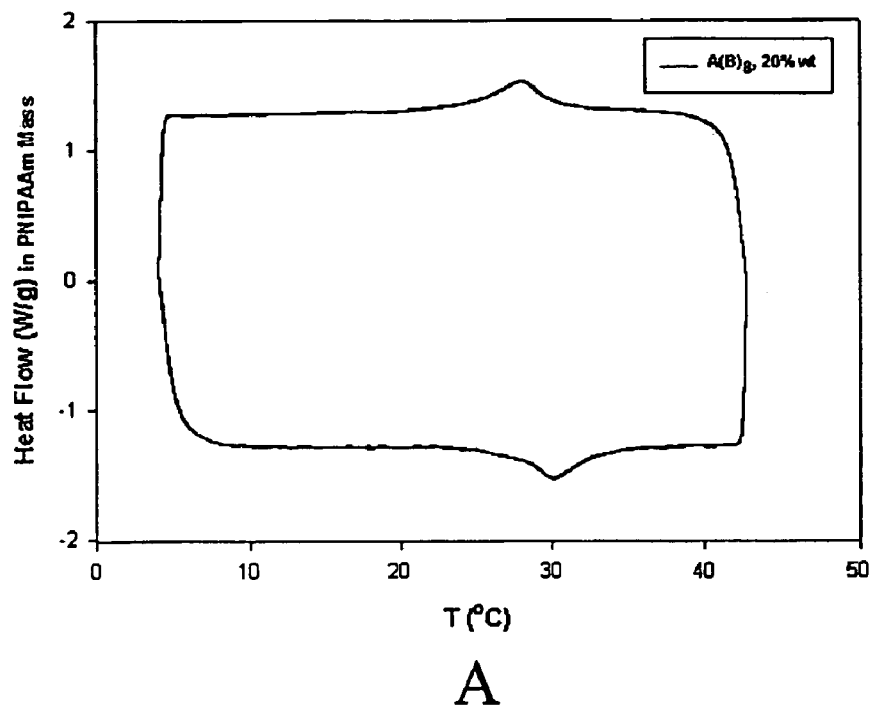
FIG. 5 shows the superposition of the DSC scans for multiple cycles for both (A) the four-arm polymer $A(B)_4$ and (B) the eight-arm polymer $A(B)_8$, both at 20% wt in water (2° C./min for 30 cycles), illustrating the full thermal reversibility of copolymers according to an embodiment of the invention.
Figure 5:
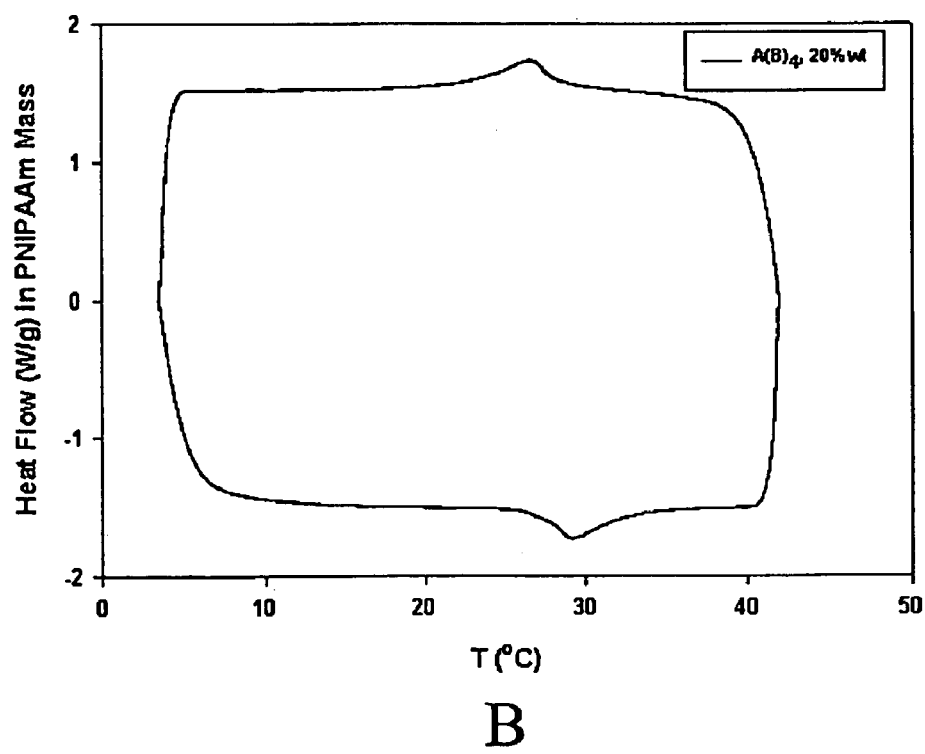

FIG. 5 shows the superposition of DSC scans for multiple cycles at 2° C./min, for aqueous compositions comprising either (A) the eight-armed polymer $A(B)_8$ or (B) the four-armed polymer $A(B)_4$, both at a concentration of 20% wt in water. All samples were subjected to cyclic heating and cooling for up to 30 cycles. The thermal behaviour of the material is completely reversible. There was a small hysteresis of 2° C. observed between heating and cooling curves.

The superposability of the scans indicates that the gelation process is completely reversible. Although the enthalpy of gel melting is identical to the enthalpy of gel formation, at a heating/cooling rate of 2° C./min, there is a difference between the peak temperatures of the heating endotherm and the cooling exotherm of about 2° C. in the scans shown in FIG. 5. The difference can be attributed to the kinetics of gelation process. At infinitely slow cooling/heating rates, the two peak temperatures should be identical. Another thermoreversible polymer hydroxypropylmethyl cellulose (HPC) has been reported to have a temperature lag of 8 to 10° C. at a much slower heating rate of 0.25° C./min (Sarkar, Journal of Applied Polymer Science, 24: 1073–1087, 1979).

$A(B)_4$ and $A(B)_8$ copolymers at 20% wt in water. A rheological scan of the one-arm copolymer (AB) composition (20% wt in water) is also provided as a comparative example. Multiple arm copolymers in general have a higher modulus than a single arm copolymer. A higher modulus means a higher number of load bearing chains per unit volume; and that is believed to be due to the very nature of having multiple aggregation blocks in one molecule. A one-arm copolymer is also different from the multiple arm copolymers in terms of its yielding behavior. Passing the yield point, the tan delta increases as stress increases, whereas the multiple arm copolymers behave otherwise. This behavior suggests a different gelation mechanism. For compositions comprising 20% wt copolymer in water, $A(B)_4$ showed the highest modulus and highest yield stress, and is thus the strongest material among the four polymers prepared.

Figure 6:
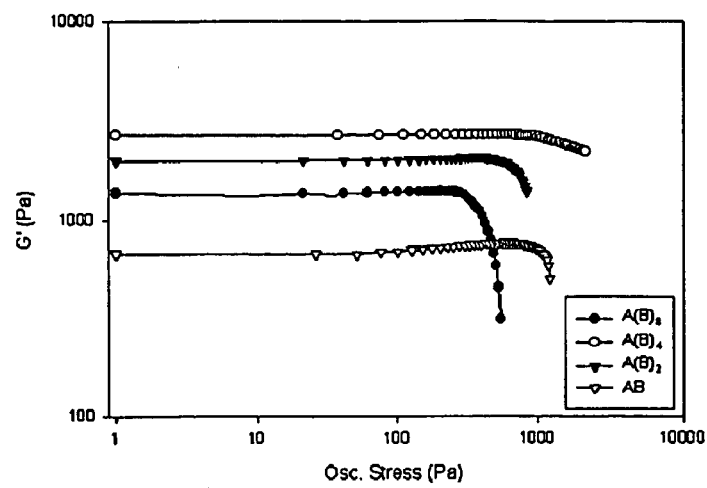
FIG. 6 illustrates parameters relating to the rheological behavior of copolymers. (A) Elastic Modulus vs. Oscillatory Stress; (B) Overall Modulus vs. Oscillatory Stress; and (C) tan delta vs. Oscillatory Stress. The tests were conducted at a frequency of 1 Hz.
Figure 6:
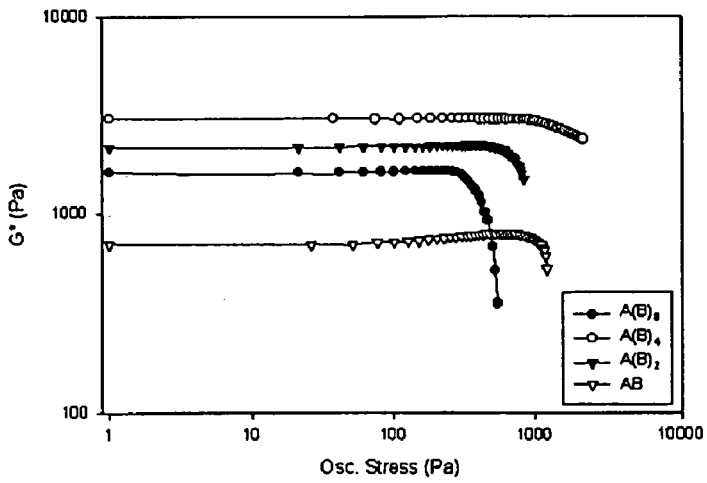
Figure 6:
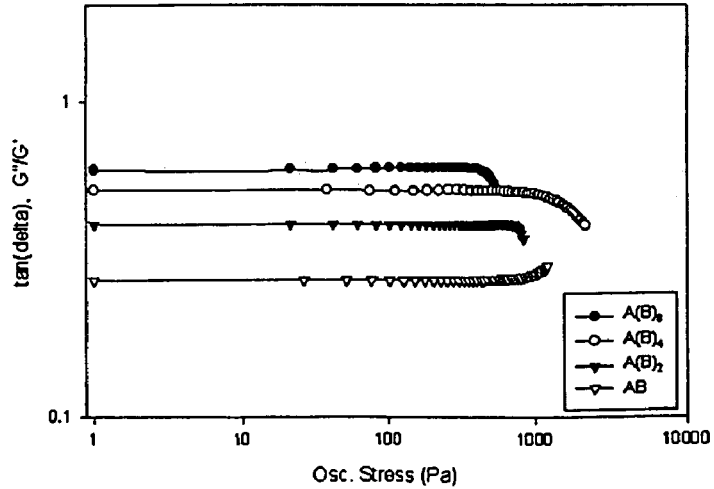

FIG. 6, part A and B show that for all four gels, G' and G* (respectively) are approximately constant over a wide range of oscillatory stress values, then decrease sharply at high stress. The stress at which the decrease occurs is different among the four gels.

Table 9 provides a summary of the constant G' and G" values at linear-viscoelastic region, which shows that G' and G" increase as the number of arms increase from 1 to 2 to 4, but then decrease upon further branching to an 8 arm architecture. The G', G" values shown in Table 9 were measured at $\omega=1$ Hz, and $\sigma=50$ Pa which is within the linear viscoelastic region of all the materials above. Values are the averages from three synthesis batches. Accordingly, loss tangent for all four gels is also seen to be approximately constant over a wide range of oscillatory stress values, but then deviate from linearity at high stress, as illustrated in FIG. 6, part C. The yield point is defined as where overall modulus, G*, deviates from linearity as illustrated in FIG. 6, part B. The corresponding stress and strain are called critical yield stress and strain.

TABLE 9

Gel Strength of Copolymers at 37° C.
G', G" at linear viscoelastic region

| Materials | G' (Pa) | G" (Pa) | Loss tan G"/G' | $\sigma_c$, Yield Stress (Pa) | $\gamma_c$, Critical Yield Strain |
|---|---|---|---|---|---|
| AB | 630 ± 130 | 180 ± 30 | 0.28 ± 0.03 | 750 ± 90 | 1.10 ± 0.15 |
| $A(B)_2$ | 2100 ± 200 | 850 ± 80 | 0.40 ± 0.04 | 600 ± 70 | 0.30 ± 0.03 |
| $A(B)_4$ | 2600 ± 250 | 1400 ± 150 | 0.53 ± 0.04 | 1000 ± 150 | 0.37 ± 0.04 |
| $A(B)_8$ | 1300 ± 150 | 800 ± 90 | 0.62 ± 0.04 | 300 ± 50 | 0.22 ± 0.03 |

The relatively small temperature hysteresis seen with these copolymers is indicative of rapid gelation kinetics compared to that of cellulose derivatives.

FIG. 6 illustrates the rheological behavior of copolymers at body temperatures. The viscoelastic and mechanical properties were evaluated by subjecting the gels at 37° C. to oscillatory stresses ($\sigma$) that ranged from 0.1 to 3,000 Pa at 1 Hz frequency, and measuring the resulting strains ($\gamma$). The elastic modulus (G'), loss modulus(G"), overall modulus ($G^* = [G'^2 + G''^2]^{1/2}$) and loss tangent, (tan $\delta \equiv G''/G'$) were then calculated.

The elastic modulus of $A(B)_2$, $A(B)_4$ and $A(B)_8$ copolymers are between 1,300 to 2,600 Pa, which makes them "hard gels", and tan delta values are between 0.4 to 0.7 which indicate that they are very much "solid-like". The examples provided in FIG. 6 are compositions of $A(B)_2$, The gelation mechanism suggests that multiple PNIPAAm segments are required in the same molecule in order for physically crosslinked hydrogel networks to be formed. Thus it is expected that the two-, four-, and eight-arm structures would form gels via a physical crosslinking mechanism, while the one-arm diblock copolymer would form a gel via the micellelar aggregation mechanism. Comparison of the rheological results for the two-, four- and eight-arm structures shows that the elastic and loss moduli in the linear viscoelastic region, as well as the yield stress and strain are all highest for the four-arm structure, indicating that the four-arm copolymer forms gels that are highest in strength, as well as deformability. Branching should have two effects on gel rheology. Increasing the number of arms should increase the degree of crosslinking in the gel via the covalent linkage of arms; hence gel strength should increase.

However, as the number of arms increases, aggregation between PNIPAAm blocks within the same molecule becomes increasingly favored over inter-molecular aggregation. Since intramolecular aggregation does not contribute to physical crosslinking, degree of physical crosslinking would decrease as branching increases beyond a certain point. The maximum in gel strength observed for the 4-arm gel may thus be explained by the counterbalancing effects of covalent crosslinking and physical crosslinking. It is also interesting to note that the loss tangent increases monotonically from 0.40 to 0.53 to 0.62 as the degree of branching increases from two to eight arms, indicating that the relative viscous component increases with the degree of branching.

A comparison of the rheological behavior of the one-arm micellar aggregate gels to the multi-arm physically crosslinked gels shows that the most striking difference between the two classes of gels is that the loss tangent decreases at high stress for the one-arm gel while for all the other gels, loss tangent increases at high stress. The contrast in trends is suggestive of a fundamental difference in the gel structure. The viscous component of the one-arm gel becomes increasingly dominant at high values of oscillatory stress, while the elastic component of the multi-arm gels become increasingly dominant.

The one-arm gel shows a significantly lower values of G' than the multi-arm gels. According to Hvidt's classification, (Hvidt, et al., Journal of Physical Chemistry, 98:12320–12328, 1994; Almgren, W Brown, S. Hvidt, Colloid and Polymer Science, 273:2, 1995), the one arm gel would be considered a "soft gel" (i.e., G'<1,000 Pa), while the others would be considered "hard gels" (i.e., G'>1,000 Pa). In contrast to the low modulus, the one arm gel has the highest critical strain among the gels, and a relatively high yield stress, lower than only the four-arm gel. With only one end tethered to PNIPAAm aggregates, PEG segments in one arm gels are more freely mobile and more readily deformable than PEG segments in multi-arm gels that are tethered at both ends. The low modulus and high critical strain of one-arm gel are a reflection of the ease of deformability. Likewise, with only one end sterically shielded by PNIPAAm aggregates, the free end of PEG segments in one-arm gels are allowed to interact with other PEG segments and form entanglements. The relatively high yield stress of one-arm gels may be the result of significant entanglement of PEG corona.

The viscosity of PEG-PNIPAAm copolymer solutions was measured at 5° C., and for a shear rate range of 0.1 to 200 $s^{-1}$. For a shear rate greater than 5 $s^{-1}$, all solutions are essentially Newtonian. The viscosity for 20% wt a one-arm diblock, two-arm triblock, four-arm star and eight-arm star are 750 cP, 950 cP, 900 cP and 700 cP respectively. All these solutions are of low enough viscosity to easily inject through a 25 G needle.

This example illustrates that block and star copolymers of PEG and PNIPAAm form liquid aqueous solutions at low temperature, and transform to relatively strong elastic gels upon heating. Multiple arm copolymers form gels via a physical crosslinking mechanism, while diblock copolymers gel by a micellar aggregation mechanism. The rheological properties of the gels are dependent on the molecular architecture, with $A(B)_4$ showed optimal properties (i.e., at 20% wt). The copolymer compositions according to the invention show relatively low injection viscosities and high gel strengths, and are therefore useful for clinical and physiological applications such as in situ drug delivery, cell encapsulation and anatomical barriers.

Example 6

Toxicity of Eight-Arm PEG/PNIPAAm Copolymer

The toxicity of a the eight-arm copolymer of PEG and PNIPPAm was tested in F-12K culture media using HIT insulinoma cells (INS-1). Solutions having 1%, and 3% concentrations of the eight-arm copolymer in culture medium were tested. F-12K culture medium included 10% fetal bovine serum. The control (0%) solution was prepared as F-12K culture medium (with 10% fetal bovine serum), but without copolymer. Multi-well plates (0.5 mL/well) were seeded with HIT cells, and either a copolymer-containing solution or the control culture medium. The wells were examined for cell viability up to 50 hours;

These dilute copolymer solutions showed no effect on cell viability in terms of % dead cells and total number of live cells compared to the control medium. The eight-arm PEG-PNIPAAm copolymer illustrated compatibility with the HIT insulinoma cells for incubations up to 50 hours. The copolymer was evaluated for toxicity at low level concentrations in culture medium so that all copolymer molecules would be freely accessible to cells. Cells would be less exposed to the polymer molecules when in gel form (ie- at higher copolymer concentrations) and it would be expected that cell toxicity of the gel form of the polymer would be considerably less than that of the dissolved form of the polymer.

Example 7

Gelation Phase Conversion for PEG/PNIPAAm Copolymer Compositions

The copolymer compositions prepared according to the invention take on a gel form at different temperatures depending on a number of parameters. A four-arm copolymer prepared according to Example 4 was examined for gelation in different solvents.

Gelation phase diagram observations were made using both a visual method and an inverted tube method. The gelation temperature is defined to be the temperature at which the composition (polymer/solvent mixture) becomes completely opaque.

Further, the inverted tube method was used to assess gelation point. Using a 1.4 cm round diameter tube, a composition is defined to be in the gel state if it does not flow after the tube has been inverted for 10 seconds. The gelation temperatures determined using the visual end point and inverted tube methods were identical.

For cell culture media or extracellular solution media, at polymer concentrations of less than about 14 wt %, compositions became turbid suspensions of white solid particles upon heating that flow easily instead of gelling. Thus, at concentrations lower than 14 weight percent, compositions of polymers in these media do not form gels. In water, no gel forms below 6 wt % polymer, and in 157 mM saline solution, no gel forms below 7 wt % polymer.

The gelation temperature increases as the concentration of copolymer in the composition decreases. Standard extracellular solution depresses the LCST. The polymer is less viscous in this solvent compared to the other solvents tested.

Figure 7:
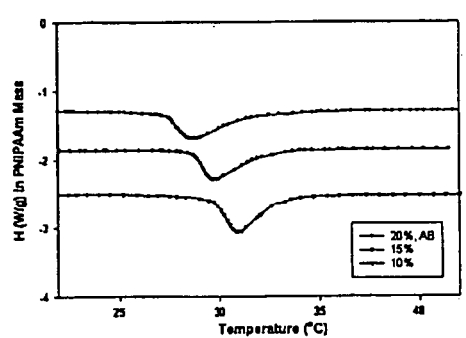
FIG. 7 illustrates thermal transition (DSC scans) of compositions containing 50/50 copolymers of PEG/PNIPAAm according to the invention at various concentrations. Comparative example (a) AB is shown relative to the inventive compositions containing (b) copolymer $A(B)_2$, (c) copolymer $A(B)_4$ and (d) copolymer $A(B)_8$.
Figure 7:
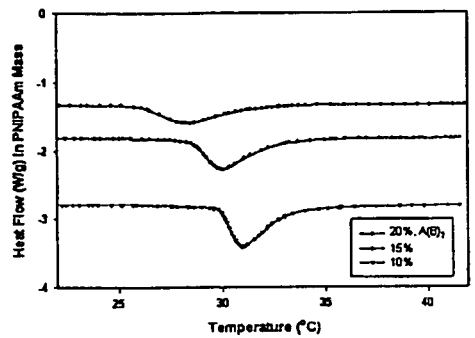
Figure 7:
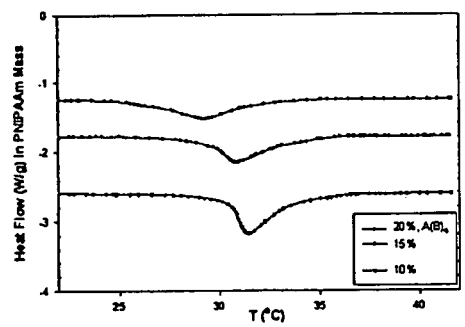
Figure 7:
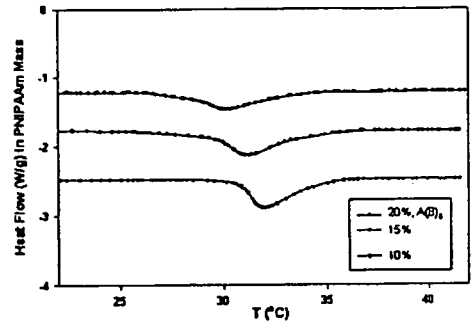
Figure 8:
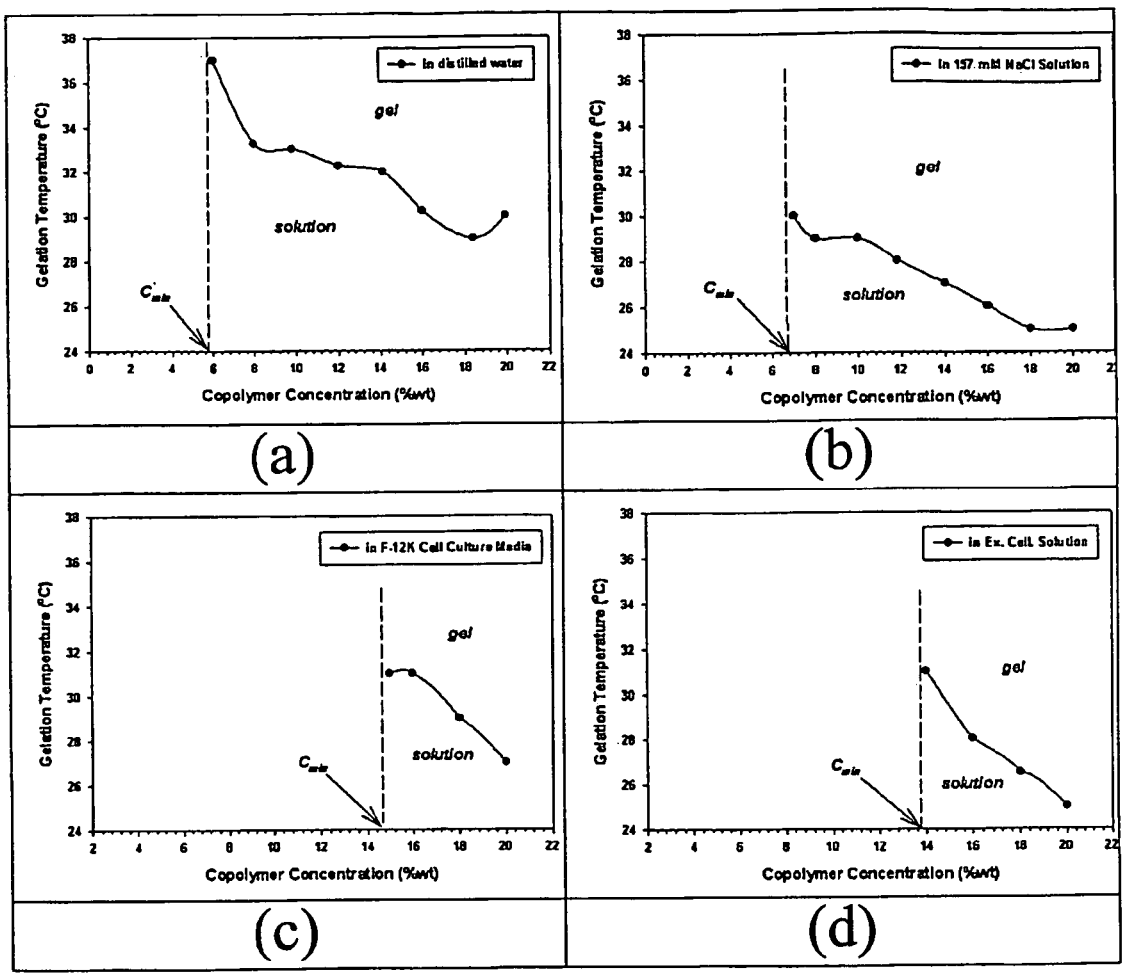
FIG. 8 provides phase diagrams PEG-PNIPAAm copolymers in (a) distilled water, (b) 157 mM NaCl solution, (c) F-12K cell culture media, and (d) extra cellular solution. $C_{min}$ is the minimum gelation concentration, below which no gel forms over the range of temperatures investigated.

FIG. 7 shows the phase diagrams of compositions comprising the copolymer in different solvents: (a) water, (b) physiological NaCl (157 mM), (c) F-12K Media, and (d) standard extracellular solution. The diagrams show temperature/concentration conditions at which the compositions (polymer/solvent mixtures) exist as solutions or gels, as well as the minimum concentration required for gel formation to occur. These data illustrate that the nature of the solvent affects the temperature at which a gel forms. A variety of different concentrations shown in the phase diagram would be appropriate for clinical and/or physiological applications of the composition.

Example 8

Copolymer of Nitrocellulose

A copolymer according to the invention is formed using nitrocellulose as arms (B) and PEG as core (A). A copolymer having either $A(B)_4$ or $A(B)_8$ architecture is formed. A gelable composition according to the invention comprises dilution of the nitrocellulose/PEG copolymer in ethanol at a concentration of about 10%.

Nitrocellulose in ethanol forms a gel upon warming. The gelation temperature depends on molecular weight and concentration. For a molecular weight of 197,000, the gelation temperature is 10° C., 5.5° C. and −20° C. for a polymer fraction of 0.5%, 1% and 4% respectively, and the theta temperature was found to be 301–310 K (Newman et al., J. Phys. Chem. 60:648–656, 1955).

Example 9

Composition Comprising Different Copolymers

A composition according to the invention is formed using copolymers having AB and $A(B)_4$ architecture, as described above in Example 4. The composition comprises a total of 15 wt % copolymer in physiological saline. The proportion of AB to $A(B)_4$ in the composition is 2:3, resulting in an average n value ($n_{avg}$) of 2.8 (or 14/5). The resulting composition is liquid at ambient temperature, and converts to a gel when injected into a subcutaneous site of a subject. This change from liquid to gel is due to a change in environmental condition, specifically the change from ambient temperature to body temperature.

Example 10

Composition Comprising Different Copolymers

A composition according to the invention is formed using a graft copolymer having $A'(B)_3$ architecture and a block copolymer having $A''(B)_4$ architecture, as described above in Example 4. In this case A' differs from A''. Each A is a PEG of differing molecular weight. However, B is the same (PNIPAAM) for both types of copolymer. The composition comprises a total of 13 wt % copolymer in cell culture media. The proportion of $A'(B)_3$ to $A''(B)_4$ in the composition is 10:3, resulting in an average n value ($n_{avg}$) of 3.23. The resulting composition is liquid at ambient temperature, and converts to a gel at a temperature below body temperature.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A gelable composition comprising a star copolymer and a solvent, the copolymer having the star-shaped structure A(B)n, wherein A is soluble in the solvent, wherein A is selected from the group consisting of polyethylene glycol (PEG), polyvinyl pyrrolidone, polyvinyl alcohol, polyhydroxyethylmethacrylate, and hyaluronic acid;

B is convertible between soluble and insoluble in the solvent depending on an environmental condition, and wherein B is selected from the group consisting of poly-N-isopropyl acrylamide (PNIPAAm), hydroxypropylmethyl cellulose and other methyl celluloses, poly(ethylene glycol vinyl ether-co-butyl vinyl ether), polymers of N-alky acrylamides, poly(amino acid)s, peptide sequences, poly(methacryloyl-L-alanine methyl ester), poly(methacryloyl-L-alanine ethyl ester) and nitrocellulose; and n is greater than 2, the composition being reversibly convertible from liquid to gel as a function of the environmental condition.

2. The composition according to claim 1, wherein the environmental condition is selected from the group consisting of temperature, pH, ionic strength, and a combination thereof.

3. The composition according to claim 1, wherein A is selected from the group consisting of polyethylene glycol (PEG), polyvinyl pyrrolidone, polyvinyl alcohol, and polyhydroxyethylmethacrylate.

4. The composition according to claim 1, wherein the environmental condition is temperature.

5. The composition according to claim 1, wherein the copolymer is present in the solvent at a level of from 5% to 50% by weight.

6. The composition according to claim 1, wherein the copolymer is present in the solvent at a level of from 10% to 25% by weight.

7. The composition according to claim 1, wherein n is 8.

8. The composition according to claim 1, wherein n greater than or equal to 4.

9. The composition according to claim 1, wherein A is polyethyleneglycol (PEG), and B is poly-N-isopropyl acrylamide (PNIPAAm).

10. The composition according to claim 1, wherein the solvent is aqueous.

11. The composition according to claim 10, wherein the solvent is selected from the group consisting of water, physiological saline and cell culture media.

12. The composition according to claim 1, additionally comprising a biologically active molecule.

13. A gelable star copolymer having the star-shaped structure A(B)n, wherein:

A is soluble in a desired solvent, and is selected from the group consisting of polyethylene glycol (PEG), polyvinyl pyrrolidone, polyvinyl alcohol, polyhydroxyethylmethacrylate, and hyaluronic acid;

B is convertible between soluble and insoluble in the desired solvent depending on an environmental condition selected from the group consisting of temperature, pH, ionic strength, and a combination thereof, and wherein B is selected from the group consisting of poly-N-isopropyl acrylamide (PNIPAAm), hydroxypropylmethyl cellulose and other methyl celluloses, poly(ethylene glycol vinyl ether-co-butyl vinyl ether), polymers of N-alky acrylamides, poly(amino acid)s, peptide sequences, poly(methacryloyl-L-alanine methyl ester), poly(methacryloyl-L-alanine ethyl ester) and nitrocellulose; and n is greater than 2; and A(B)n is reversibly convertible from liquid to gel in the solvent as a function of the environmental condition.

14. The gelable copolymer according to claim 13, additionally comprising a degradable linker (C) between A and B.

15. The copolymer according to claim 13, wherein A is degradable.

16. The copolymer according to claim 13, additionally comprising a biologically active compound (D) bound to component A or B.

* * * * *